(12) United States Patent
Guo et al.

(10) Patent No.: US 11,597,922 B2
(45) Date of Patent: Mar. 7, 2023

(54) METHOD FOR ANALYZING IMPURITIES OF OLIGONUCLEOTIDE SEQUENCE BASED ON HIGH-THROUGHPUT SEQUENCING AND APPLICATION

(71) Applicants: SUZHOU GENESCI CO., LTD, Suzhou (CN); SUZHOU GENEPHARMA CO., LTD, Suzhou (CN)

(72) Inventors: Liangrang Guo, Suzhou (CN); Peizhuo Zhang, Suzhou (CN); Lei Yu, Suzhou (CN)

(73) Assignees: SUZHOU GENESCI CO., LTD, Suzhou (CN); SUZHOU GENEPHARMA CO., LTD, Suzhou (CN)

( * ) Notice: Subject to any disclaimer, the term of this patent is extended or adjusted under 35 U.S.C. 154(b) by 413 days.

(21) Appl. No.: 16/648,529

(22) PCT Filed: Aug. 23, 2018

(86) PCT No.: PCT/CN2018/101878
§ 371 (c)(1),
(2) Date: Mar. 18, 2020

(87) PCT Pub. No.: WO2019/052322
PCT Pub. Date: Mar. 21, 2019

(65) Prior Publication Data
US 2021/0095270 A1    Apr. 1, 2021

(30) Foreign Application Priority Data
Sep. 18, 2017  (CN) .......................... 201710840332.4

(51) Int. Cl.
C12N 15/10    (2006.01)
C12Q 1/6806   (2018.01)
C12Q 1/6869   (2018.01)

(52) U.S. Cl.
CPC ....... *C12N 15/1093* (2013.01); *C12Q 1/6806* (2013.01); *C12Q 1/6869* (2013.01)

(58) Field of Classification Search
None
See application file for complete search history.

(56) References Cited

FOREIGN PATENT DOCUMENTS

| CN | 105463585 | | 4/2016 | |
|---|---|---|---|---|
| CN | 105463585 | A | 4/2016 | |
| CN | 105754995 | | 7/2016 | |
| JP | 2006-166907 | A | 6/2006 | |
| WO | 2015054247 | A1 | 4/2015 | |
| WO | 2015/111209 | A1 | 7/2015 | |
| WO | 2016010856 | A1 | 1/2016 | |
| WO | WO-2016037537 | A1 * | 3/2016 | ......... C12N 15/1093 |

OTHER PUBLICATIONS

Gansauge et al., "Single-stranded DNA library preparation for the sequencing of ancient or damaged DNA," Nat. Protoc. 2013, 8: 737-748. (Year: 2013).*
Chen, Su-Hong et al.; "Sequence confirmation of phosphorothioate antisense oligodeoxy nucleotides using direct Sanger sequencing reactions", Institute of Radiation Medicine—Academy of Military Medical Sciences, Beijing, China, Oct. 2004; vol. 28, No. 5; pp. 442-497. (See English Abstract).
First Office Action issued in corresponding Chinese Patent Application No. 201710840332.4; dated Jul. 5, 2021; 9 pgs.
International search report dated Nov. 9, 2018 from corresponding application No. PCT/CN2018/101878.
Chen et al., "Sequence Confirmation of Phosphorothioate Antisense Oligodeoxynucleotides Using Direct Sanger Sequencing Reactions", Bulletin of the Academy of Military Medical Sciences, vol. 28, No. (5), Oct. 31, 2004 (Oct. 31, 2004), pp. 442-445 and 497.
Gansauge, Marie-Theres, et al., "Single-stranded DNA library preparation from highly degraded DNA using T4 DNA ligase", Nucleic Acids Research, Jan. 23, 2017, DOI: 10.1093/nar/gkx033; 10 pgs.
Gansauge, Marie-Theres, et al., "Single-stranded DNA library preparation for the sequencing of ancient or damaged DNA", Nature Protocols, vol. 8, No. 4, Mar. 14, 2013 (Mar. 14, 2013), pp. 737-748.
Kugelman, Jeffrey R., et al. "Error baseline rates of five sample preparation methods used to characterize RNA virus populations", PLOS ONE, vol. 12, No. 2, Feb. 9, 2017, p. 1-13; Retrieved from the Internet: URL:https://www.ncbi.nlm.nih.gov/pmc/articles/PMC5300104/pdf /pone.0171333.pdf.

(Continued)

*Primary Examiner* — Kaijiang Zhang
(74) *Attorney, Agent, or Firm* — Hauptman Ham, LLP

(57) ABSTRACT

The present invention provides a method for analyzing impurities of an oligonucleotide sequence based on high-throughput sequencing. The method of the present invention comprises the following steps: constructing a high-throughput sequencing library for analysis of impurities of an oligonucleotide sequence; subjecting the high-throughput sequencing library to high-throughput sequencing, and analyzing the nucleotide sequence components according to the sequencing results; the sequence of the extension primer used in the construction of the high-throughput sequencing library consisting of the DNA molecule set forth in positions 1-22 of SEQ ID NO: 2 and N bases (A, T, C or G) in sequence; and N being an integer greater than or equal to 6. It is proved by experiments that the method for analyzing impurities of an oligonucleotide sequence based on high-throughput sequencing of the present invention can quickly, accurately, and comprehensively analyze the purity and content of each component in the oligonucleotide sequence.

10 Claims, 3 Drawing Sheets
Specification includes a Sequence Listing.

(56) References Cited

OTHER PUBLICATIONS

Supplementary European Search Report issued in EP Application No. 18857038; dated Apr. 9, 2021; 3 pgs.
Notice of Reasons for Refusal issued in corresponding Japanese Application No. 2020-537274; dated May 25, 2021; 6 pgs.

\* cited by examiner

METHOD FOR ANALYZING IMPURITIES OF OLIGONUCLEOTIDE SEQUENCE BASED ON HIGH-THROUGHPUT SEQUENCING AND APPLICATION

RELATED APPLICATIONS

The present application is a National Phase of International Application Number PCT/CN2018/101878, filed Aug. 23, 2018, and claims the priority of China Application No. 201710840332.4, filed Sep. 18, 2017.

INCORPORATION BY REFERENCE

The sequence listing provided in the file entitled C6351-020_SEQUENCE_LISTING_v2.txt, which is an ASCII text file that was created on Jul. 15, 2020, and which comprises 5,079 bytes, is hereby incorporated by reference in its entirety.

TECHNICAL FIELD

The present invention belongs to the field of biotechnology, and particularly relates to a method for analyzing impurities of an oligonucleotide sequence based on high-throughput sequencing and application.

BACKGROUND ART

In recent years, more and more pharmaceutical companies at home and abroad have been involved in gene medicines, investing heavily in the development of new gene medicines to combat various diseases. Antisense oligodeoxynucleotide technology is a treatment method that uses artificially synthesized or biosynthesized DNA or RNA that is complementary to RNA to block and inhibit the expression of genes related to disease occurrence, which can be used to treat tumors or genetic diseases caused by gene mutations.

Antisense technology is a new method of drug development. The drugs developed using this technology are called antisense drugs and involve antisense DNA, antisense RNA, and ribozyme. According to the principle of nucleic acid hybridization, antisense drugs can hybridize with specific genes and interfere with the production of pathogenic proteins at the gene level, i.e., interfere with the transmission of genetic information from nucleic acids to proteins. Traditional drugs mainly act directly on the pathogenic proteins themselves, while antisense drugs act on the genes that produce the proteins. Compared with traditional drugs, antisense drugs have higher selectivity and efficiency and can be widely used in the treatment of a variety of diseases, such as infectious diseases, inflammation, cardiovascular diseases and tumors.

Gene therapy refers to the introduction of foreign normal genes into target cells to correct or compensate for diseases caused by gene defects and abnormalities, so as to achieve therapeutic purposes. Broadly speaking, gene therapy can also include measures and new technologies to treat certain diseases at the DNA level.

Antisense DNA mainly refers to antisense oligodeoxynucleotide (AS-ODN). AS-ODN is a short single-stranded DNA fragment, which is artificially synthesized and complementary to one or more sites (complementary regions) of the target gene mRNA and can inhibit or reduce the expression of the target gene. AS-ODN can act on different targets: binding to double-stranded DNA to regulate transcription; binding to mRNA precursors or splice junctions to inhibit splicing of mRNA precursors and affect the transport of spliced mRNA from the nucleus to the cytoplasm; binding to mRNA in the cytoplasm to block translation; binding to specific proteins to regulate gene expression.

Since antisense DNA is an artificially synthesized sequence, there are base insertions and deletions during the synthesis process, resulting in a large amount of impurities in the synthesized DNA, and the synthesized sequence needs to be purified for pharmaceutical use, so it is necessary to analyze and confirm the purified sequence components. However, there is currently no good solution for the analysis of single-stranded oligonucleotide sequences.

SUMMARY OF THE INVENTION

The technical problem to be solved by the present invention is how to quickly, accurately and comprehensively analyze the composition and purity and/or content of each component sequence in an artificially synthesized oligonucleotide sequence.

In order to solve the above technical problem, the present invention first provides a method for constructing a high-throughput sequencing library for analysis of impurities of an oligonucleotide sequence.

The method for constructing a high-throughput sequencing library for analysis of impurities of an oligonucleotide sequence provided by the present invention comprises the following steps:

1) adding a poly tail to the 3' end of an oligonucleotide sequence to be detected to obtain a poly-tailed product;
2) performing reverse extension and amplification on the poly-tailed product to obtain a reverse extension and amplification product;
the primers used for the reverse extension and amplification consisting of the oligonucleotide to be detected and an extension primer;
the extension primer sequence consisting of the DNA molecule set forth in positions 1-22 of SEQ ID NO: 2 and N bases (A, T, C or G) in sequence; and N being an integer greater than or equal to 6;
3) precipitating the reverse extension and amplification product to obtain a precipitated product;
4) performing end repair, A-tailing reaction, adapter ligation and PCR amplification on the precipitated product sequentially to obtain a high-throughput sequencing library.

In the above method, the length of the oligonucleotide can be 8-120 bp. The oligonucleotide can be single-stranded DNA or double-stranded DNA. In a specific embodiment of the present invention, the oligonucleotide is single-stranded DNA, and its nucleotide sequence is SEQ ID NO: 5 with a size of 21 bp.

In the above method, in step 1), the poly tail can be a poly A tail, a poly G tail, a poly C tail, or a poly T tail; in a specific embodiment of the present invention, the poly tail is a poly A tail;
the method of adding a poly tail to the 3' end of an oligonucleotide sequence to be detected is as follows: 1.5 μL of terminal transferase, 1 μL of the oligonucleotide to be detected, 0.5 μL of dATP (or dTTP or dCTP or dGTP) (25 μM), 4 μL of 5×TdT Buffer and nuclease-free water are mixed to obtain a reaction system (total volume is 20 μL). The final concentration of the oligonucleotide to be detected in the reaction system is 5 μM.

In the above method, in step 2), N can be any integer greater than or equal to 6. In a specific embodiment of the present invention, N is specifically 20. When N is 20, the extension primer sequence is the DNA molecule set forth in SEQ ID NO: 1 or the DNA molecule set forth in SEQ ID NO: 2 or the DNA molecule set forth in SEQ ID NO: 3 or the DNA molecule set forth in SEQ ID NO: 4. In a specific embodiment of the present invention, the extension primer sequence is the DNA molecule set forth in SEQ ID NO: 1.

The reverse extension and amplification reaction system (total volume is 50 μL) consists of 25 μL of 2×Phata Max Buffer, 2 μL of dNTPS (10 mM), 2 μL of the extension primer, 1 μL of the oligonucleotide to be detected, 1 μL of DNA polymerase I and nuclease-free water. The final concentration of the extension primer in the reverse system is 4 μM; the final concentration of the oligonucleotide to be detected in the reverse system is 2 μM.

In the above method, in step 3), the method used for the precipitation is sodium acetate precipitation; the method of subjecting the reverse extension and amplification product to sodium acetate precipitation is as follows:
3a) adding sodium acetate, absolute ethanol and glycogen to the reverse extension and amplification product;
3b) centrifuging, discarding the supernatant and collecting the precipitate;
3c) adding ethanol to the precipitate, centrifuging, discarding the supernatant, and collecting the precipitate.

In step 3a), 1/10 volume of sodium acetate, 2.5 volumes of absolute ethanol and 1 μL of glycogen are added to the reverse extension and amplification product; the pH of the sodium acetate is 5.2; the concentration of the glycogen is 20 mg/mL;
in step 3b), the centrifugation conditions are 12000 rpm for 30 minutes at 4° C.;
in step 3c), the centrifugation conditions are 12000 rpm for 5 minutes at 4° C.; and the ethanol is 80% aqueous ethanol solution by volume;
further included between steps 3a) and 3b) is a step of placing at −80° C. for 30 minutes; step 3c) is repeated once.

In the above method, in step 4), the method of performing end repair, A-tailing reaction, adapter ligation and PCR amplification on the precipitated product sequentially is as follows:
4a) performing end repair and A-tailing reaction on the precipitated product to obtain a repaired product;
4b) ligating an adapter to the repaired product to obtain an adapter-ligated product;
4c) performing PCR amplification on the adapter-ligated product to obtain an amplification product, i.e., a high-throughput sequencing library for analysis of impurities of an oligonucleotide sequence.

In step 4a), the method of performing end repair and A-tailing reaction on the precipitated product is as follows: 15 μL of the precipitated product, 3 μL of 10×End Repair Buffer, 2 μL of T4 DNA polymerase, 2 μL of T4 Polynucleotide Kinase (T4PNK), 0.5 μL of Klenow DNA polymerase 1, 0.5 μL of Bst DNA Pol I large Fragment and 7 μL of nuclease-free water are mixed and reacted.

In step 4b), the method of ligating an adapter to the repaired product is as follows: 30 μL of the repaired product, 15 μL of 10×T4 DNA Ligase Buffer, 2 μL of T4 DNA Ligase, 2 μL of Y-shape adapter and 1 μL of nuclease-free water are mixed and reacted.

In step 4c), the method of performing PCR amplification on the adapter-ligated product is as follows: 5 μL of the adapter-ligated product, 2 μL of each primer, 1 μL of dNTP mix (10 mM), 25 μL of 2×Phanta Max Buffer, 1 μL of Phanta Max Super Fide DNA polymerase and 14 μL of nuclease-free water are mixed and reacted. The final concentration of each primer in the reaction system is 1 μM.

Further included between steps 4b) and 4c) is a purification step, and the purification can be performed by using magnetic beads.

Step 4c) is followed by a purification step, and the purification can be performed by using a silica gel column.

In order to solve the above technical problem, the present invention further provides a product.

The product of the present invention is any one of the following a1)-a3):
a1) the extension primer;
a2) a PCR reagent containing the extension primer of a1):
a3) a kit containing the extension primer of a1) or the PCR reagent of a2).

In the above product, the final concentration of the extension primer in the PCR reagent is 0.1 to 100 μM. In a specific embodiment of the present invention, the final concentration of the extension primer in the PCR reagent is 100 μM.

Use of the above product for constructing a high-throughput sequencing library for analysis of impurities of an oligonucleotide sequence also belongs to the protection scope of the present invention.

Use of the above product for analyzing impurities of an oligonucleotide sequence also belongs to the protection scope of the present invention.

In order to solve the above technical problem, the present invention further provides a method for analyzing impurities of an oligonucleotide sequence.

The method for analyzing impurities of an oligonucleotide sequence provided by the present invention comprises the following steps:
(1) constructing a high-throughput sequencing library for analysis of impurities of an oligonucleotide sequence according to the above method;
(2) subjecting the high-throughput sequencing library to high-throughput sequencing, and analyzing the nucleotide sequence components according to the sequencing results.

In order to solve the above technical problem, the present invention finally provides a new use of the above method.

The present invention provides use of the above method for analyzing components of an artificially synthesized antisense oligonucleotide sequence for gene therapy.

The present invention further provides use of the above method for analyzing the purity and/or content of each component in an artificially synthesized antisense oligonucleotide sequence for gene therapy.

It is proved by experiments that the method for analyzing impurities of an oligonucleotide sequence based on high-throughput sequencing of the present invention can quickly, accurately, and comprehensively analyze the purity and content of each component in an oligonucleotide sequence.

DETAILED DESCRIPTION OF THE INVENTION

Figure 1:
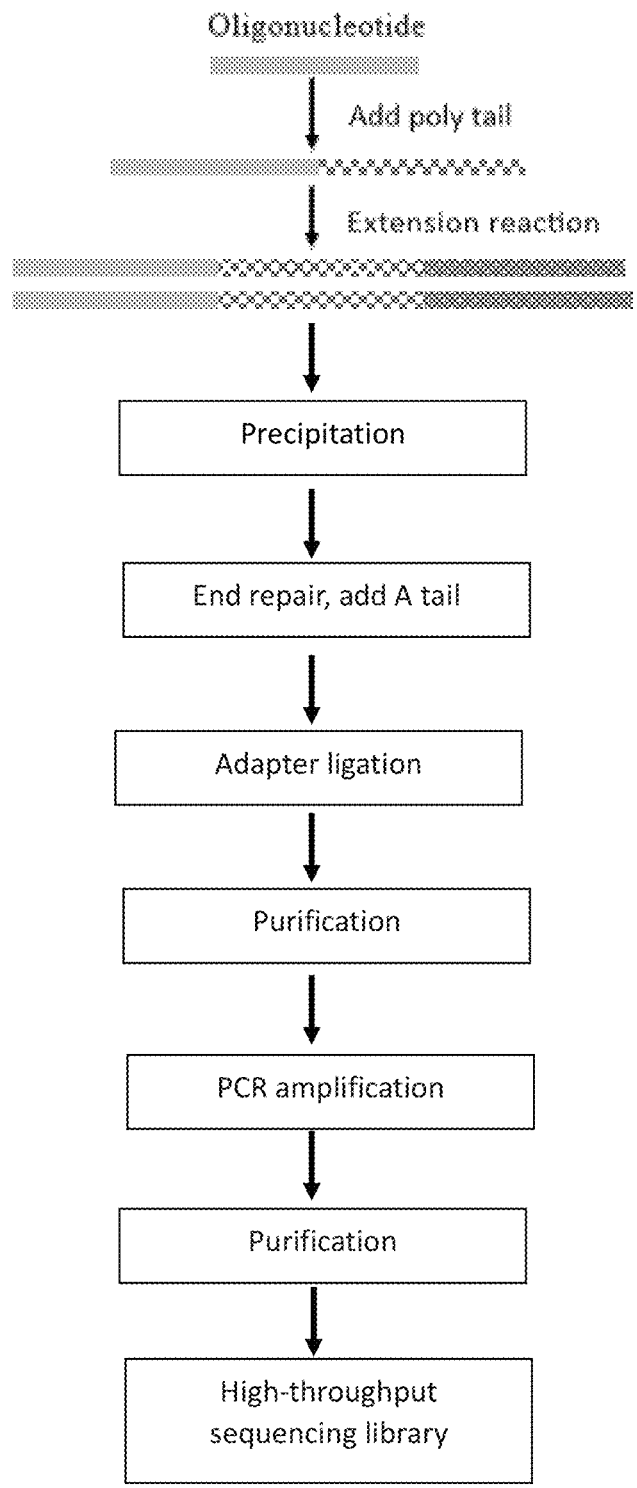
FIG. 1 is a flowchart of a method for analyzing impurities of an oligonucleotide sequence based on high-throughput sequencing.

Unless otherwise specified, the experimental methods used in the following example are conventional methods.

The materials, reagents, etc. used in the following example are available commercially, unless otherwise specified.

In the following example, T4 DNA polymerase is a product from NEB (Beijing) LTD and the catalog number is M0203L. Both DNA Polymerase I and Large (Klenow) Fragment are products from NEB, and the catalog number is M0210S. Hereinafter, DNA Polymerase I and Large (Klenow) Fragment are referred to as DNA polymerase I. T4 Polynucleotide Kinase is a product from NEB, and the catalog number is M0201. Klenow DNA polymerase I and Bst DNA Pol I large Fragment are products from NEB, and the catalog number is M0275. T4 DNA Ligase is a product from NEB, and the catalog number is M0202L. Terminal transferase is a product from Thermo Fisher Scientific (China) Co., Ltd., and the catalog number is EP0162. Deoxyadenosine triphosphate is a product from Thermo Fisher Scientific (China) Co., Ltd., and the catalog number is 10216018. Phanta Max Super Fide DNA Polymerase is a product from Vazyme Biotech Co., Ltd., and the catalog number is P505.

The formulation of 10×End Repair Buffer in the following example is: the solutes and their concentrations are: 900 mM $MgCl_2$, 30 mM DTT, 10 mM ATP, 1 μg/μL BSA and 4 mM dNTPs; the solvent is 500 mM Tris-HCl buffer (pH 8.3).

Example 1. A Method for Analyzing Impurities of an Oligonucleotide Sequence Based on High-Throughput Sequencing I. Adding Poly Tail to Oligonucleotide 1. A poly A tail was added to the 3' end of the oligonucleotide sequence, and a tailing reaction system was prepared according to each reagent and its addition amount in Table 1. The oligonucleotide sequence is as follows: 5'-CAGAGCAGCTTGTCTTTCTTC-3' (SEQ ID NO: 5). The oligonucleotide sequence was synthesized by Shanghai Generay Biotech Co., Ltd.

TABLE 1

| Tailing reaction system | |
|---|---|
| Reagent | Addition amount (μL) |
| Nuclease-free water | 13 |
| Oligonucleotide (100 μM) | 1 |
| dATP (25 μM) | 0.5 |
| 5 × TdT Buffer | 4 |
| Terminal transferase | 1.5 |
| Total volume | 20 μL |

2. The reaction was performed at 37° C. for 25 min.
3. The reaction mixture was incubated at 70° C. for 10 min to inactivate the terminal transferase.

II. Reverse Extension and Amplification

1. Each of the reagents shown in Table 2 was added to the reaction product obtained in above step 1 to prepare a reverse extension and amplification system.

TABLE 2

| Reverse extension and amplification system | |
|---|---|
| Reagent | Addition amount (μL) |
| Nuclease-free water | 19 |
| 2 × Phanta Max Buffer | 25 |
| dNTPS (10 mM) | 2 |
| Extension primer extpT (100 μM) | 2 |
| Oligonucleotide (100 μM) | 1 |
| DNA Polymerase I | 1 |
| Total volume | 50 |

The sequence of the extension primer extpT is as follows:

(SEQ ID NO: 1)
5'-GAGACACGAATAGACGGCACGATTTTTTTTTTTTTTTTTTTT-3'.

2. The reverse extension and amplification system prepared in step 1 was placed on a PCR instrument and the reaction procedure shown in Table 3 was performed.

TABLE 3

| Reverse extension and amplification procedure | |
|---|---|
| Segment 1 | 95° C. for 30 s |
| Segment 2 | 95° C. for 30 s |
| (20 cycles) | 60° C. for 15 s |
|  | 72° C. for 30 s |
| Segment 3 | 72° C. for 10 min |
| Segment 4 | Stored at 10° C. |

III. Sodium Acetate Precipitation

Figure 2:
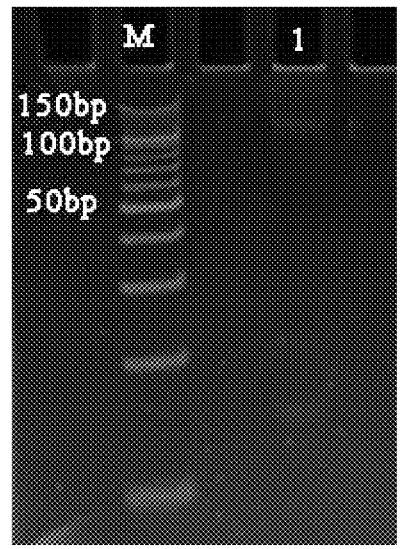
FIG. 2 shows the results of electrophoresis detection of the product precipitated with sodium acetate.

1. The product obtained in step 11 was added with 1/10 volume of sodium acetate (pH5.2), 2.5 volumes of absolute ethanol and 1 μL of glycogen with a concentration of 20 mg/mL.
2. The mixture was kept at −80° C. for 30 minutes.
3. The mixture was then centrifuged at 12000 rpm for 30 minutes at 4° C. and the supernatant was discarded and the precipitate was collected.
4. 1 mL of 80% aqueous ethanol solution was added to the precipitate, and then centrifuged at 12000 rpm for 5 minutes at 4° C. The supernatant was discarded and the precipitate was collected.
5. Step 4 was repeated once.
6. The precipitate was dried at room temperature and added with 30 μL of TE to dissolve.
7. The precipitation product was detected. The specific steps were as follows: a 12% PAGE gel was prepared, the precipitation product was loaded and electrophoresed at 200 V for 40 minutes, stained in a dark box for 10 minutes, and photographed in a gel imaging system. The results of electrophoresis detection are shown in FIG. 2.

IV. End Repair

1. An end repair reaction system was prepared according to each reagent and its addition amount in Table 4. After preparation, the reagents were mixed and subjected to instantaneous centrifugation.

TABLE 4

End repair reaction system.

| Reagent | Addition amount (μL) |
| --- | --- |
| Nuclease-free water | 7 |
| 10 × End Repair Buffer | 3 |
| T4 DNA Polymerase | 2 |
| T4 Polynucleotide Kinase (T4 PNK) | 2 |
| Klenow DNA polymerase I | 0.5 |
| Bst DNA Pol I large Fragment | 0.5 |
| The product of step III | 15 |
| Total volume | 30 |

2. The end repair reaction system in step 1 was placed on a PCR instrument and the reaction procedure shown in Table 5 was performed.

TABLE 5

PCR reaction procedure

| Segment 1 | 20 □ for 30 min |
| --- | --- |
| Segment 2 | 65 □ for 30 min |
| Segment 3 | Stored at 10° C. |

V. Adapter Ligation

1. An adapter ligation reaction system was prepared according to each reagent and its addition amount in Table 6. After preparation, the reagents were mixed and subjected to instantaneous centrifugation.

TABLE 6

Adapter ligation reaction system

| Reagent | Addition amount (μL) |
| --- | --- |
| End repair product | 30 |
| Nuclease-free water | 11 |
| 10 × T4 DNA Ligase Buffer | 5 |
| Y-shape adapter (40 μM) | 2 |
| T4 DNA Ligase | 2 |
| Total volume | 50 |

The above Y-shape adapter consists of UAF and AI5, and their sequences are as follows:

```
UAF (the underlined base is thio-modified):
5-AATGATACGGCGACCACCGAGATCTACACTCTTTCCCTACACGACGC

TCTTCCGATCT;

AI5 (the underlined base is phosphate-modified):
5-GATCGGAAGAGCACACGTCTGAACTCCAGTCACACAGTGATCTCGTA

TGCCGTCTTCTGCTTG.
```

The above Y-shape adapter sequence was synthesized by Shanghai Generay Biotech Co., Ltd. The concentration of each adapter in the adapter ligation reaction system was 1.6 μM.

2. The adapter ligation reaction system was placed on a PCR instrument at 16° C. for 2 hours to obtain an adapter-ligated product.

VI. Purification of Adapter-Ligated Product

1. Ampure XP magnetic beads (Agencourt AMPure XP Kit produced by Beckman Coulter, Inc., catalog number: A63880) were thoroughly mixed by shaking;

2. 1×Ampure XP magnetic beads was added to the ligation product obtained in above step V, mixed 10 times with a pipette, and kept at room temperature for 1 min;

3. The mixture was placed on a magnetic stand for 5 min and the supernatant was discarded.

4. 200 μL of freshly prepared 80% aqueous ethanol solution was added to the magnetic beads, placed at room temperature for 30 s, and the supernatant was discarded;

5. The above step 4 was repeated once;

6. 50 μL of 10 mM Tris-HCl (pH 8.0) was added for elution, and the supernatant was transferred to a new centrifuge tube;

7. One volume of magnetic beads was added and mixed 10 times with a pipette, and kept at room temperature for 1 min;

8. 200 μL of freshly prepared 80% aqueous ethanol solution was added to the magnetic beads and kept at room temperature for 30 s, and the supernatant was discarded;

9. The above step 8 was repeated once;

10. The lid was opened and the tube was kept at room temperature for 10 min;

11. 50 μL of 10 mM Tris-HCl (pH 8.0) was added and mixed with a pipette, and kept at room temperature for 1 min:

12. The tube was placed on a magnetic stand for 5 min, and the supernatant was transferred to a new centrifuge tube, and the purified adapter-ligated product was obtained.

VII. PCR Amplification of Adapter-Ligated Product

1. Each of the reagents in Table 7 was added to the purified adapter-ligated product (the addition amounts were also shown in Table 7) to prepare a PCR amplification system.

TABLE 7

PCR amplification system

| Reagent | Addition amount (μL) |
| --- | --- |
| Nuclease-free water | 14 |
| mpF (25 μM) | 2 |
| mpRI5 (25 μM) | 2 |
| dNTP mix (10 mM) | 1 |
| 2 × Phanta Max Buffer | 25 |
| Phanta Max Super Fide DNA Polymerase | 1 |

The sequence of the primer mPF is as follows (synthesized by Shanghai Generay Biotech Co., Ltd):

```
AATGATACGGCGACCACCGAGATCTACACTCTTTCCCTACACGACGCTC

TTCCGATCT;
``` the sequence of the primer mRPI5 is as follows (synthesized by Shanghai Generay Biotech Co., Ltd): CAAGCAGAA-GACGGCATACGAGATCACTGTGTGACTG-GAGTTCAGACGTGTGC TCTTCCGATCT. In the above primer sequence, the underlined base is thio-modified.

2. The mixture was divided into PCR tubes in 45 μL/tube and then 5 μL of the ligation product was added.

Figure 3:
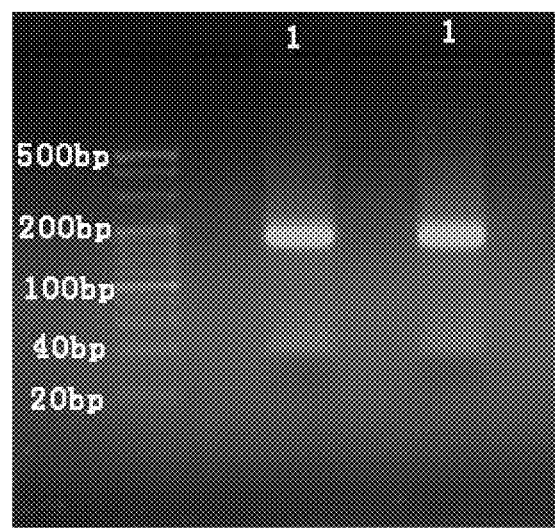
FIG. 3 shows the results of electrophoresis detection of the PCR amplification product.

3. The PCR amplification system was placed in a PCR instrument, and the amplification was performed according to the PCR reaction procedure shown in Table 8, to obtain PCR amplification product. The PCR amplification product was subjected to gel electrophoresis detection, and the results are shown in FIG. 3.

TABLE 8

| PCR reaction procedure | |
| --- | --- |
| Segment 1 | 94 □ for 3 min |
| Segment 2 | 94 □ for 30 s |
| (20 cycles) | 60 □ for 30 s |
| | 72 □ for 30 s |
| Segment 3 | 72 □ for 10 min |
| Segment 4 | Stored at 4 □ |

Figure 4:
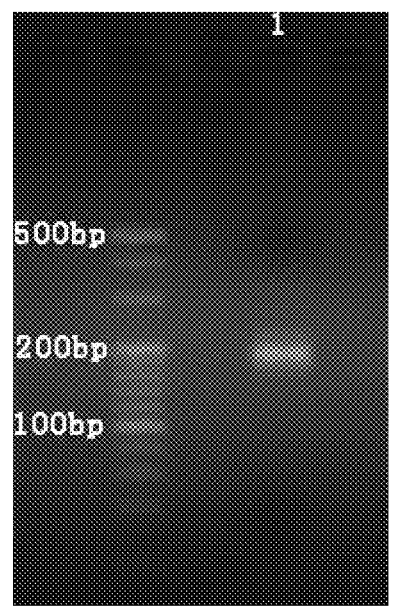
FIG. 4 shows the results of electrophoresis detection of the purified PCR amplification product.
Figure 5:
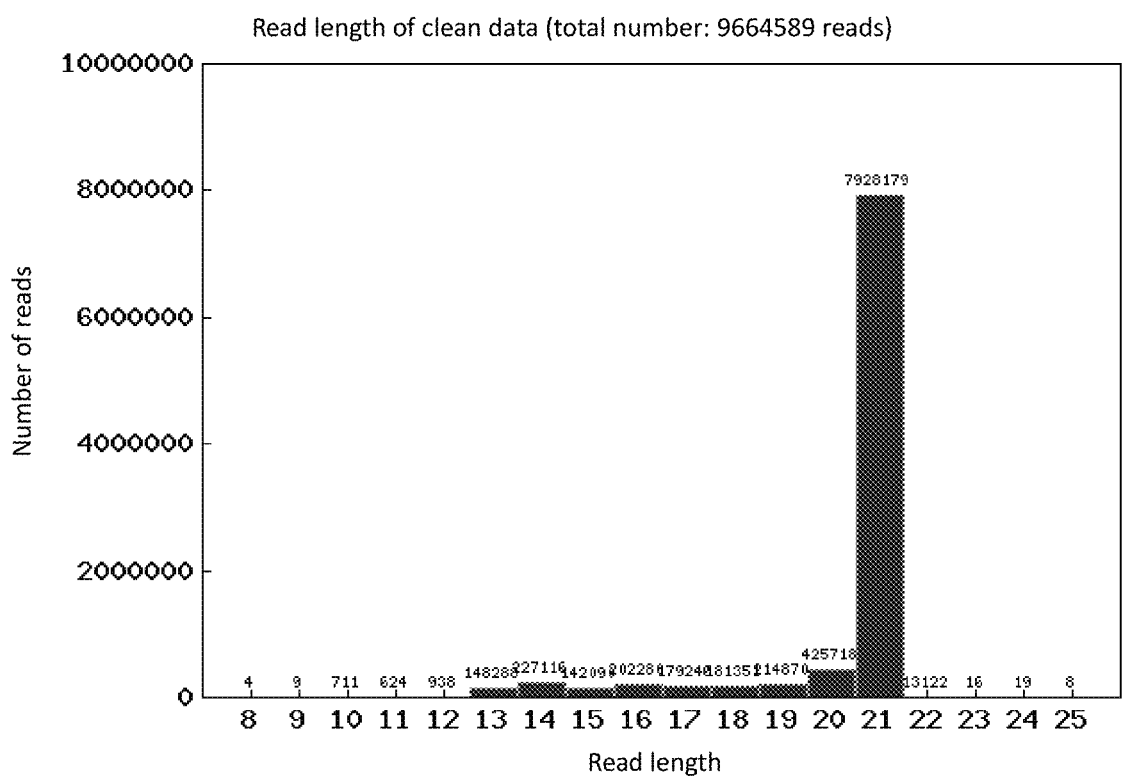
FIG. 5 shows the results of high-throughput sequencing data analysis.

VIII. Purification of PCR Amplification Product
1. The required bands in the above electrophoresis were cut out, and gel recovery was performed using the Agarose Gel DNA Recovery Kit (centrifugal column type: GK2042-50) from Shanghai Generay Biotech Co., Ltd.
2. 400 μL of Binding Solution was added to the gel and placed in a 50° C. water bath until the gel block was dissolved.
3. The mixture was shaken once every 2 minutes during this period.
4. The dissolved gel block was transferred to a silica gel column, kept at room temperature for 2 min, and centrifuged at 6000 rpm for 1 min, and the waste solution was discarded.
5. 500 μL of Washing Solution was added to the silica gel column, and kept at room temperature for 3 min.
6. The mixture was centrifuged at 12000 rpm for 1 min and the waste solution was discarded.
7. Step 6 was repeated once.
8. The mixture was centrifuged at 12000 rpm for 1 min and the silica gel column was transferred to a new 1.5 mL centrifuge tube.
9. 30 μL of nuclease-free water was added to the silica gel column, and kept at room temperature for 2 min.
10. The mixture was centrifuged at 12000 rpm for 1 min and the supernatant was collected to obtain a purified PCR amplification product. The purified PCR amplification product was subjected to electrophoresis detection, and the results are shown in FIG. 4, wherein, M: 20 bp DNA Ladder; 1: library gel recovery product. As can be seen from the figure, a high-throughput sequencing library was successfully obtained.

IX. High-Throughput Sequencing and Data Analysis
1. High-Throughput Sequencing
The library constructed in step VIII was sequenced using the Hiseq 3000 platform in a single-end 150 bp sequencing mode.
2. Analysis of High-Throughput Sequencing Results
The trimmomatic-0.33 software (the URL of the trimmomatic-0.33 software is as follows: www.usadellab.org/cms/index.php?page=trimmomatic) was used to remove low-quality bases at the 3' end of the read, and the self-written per script ExtractValid.pl was used to extract the forward sequencing reads containing the adapter, the cutadapt1.2.1 software (the URL of the cutadapt1.2.1 software is as follows: github.com/marcelm/cutadapt/releases/tag/v1.2.1) was used to remove the Poly A adapter from the reads, the self-written per script FilterTN.pl was used to remove the reads containing N and Poly T adapters, the self-written perl script trim_polytail.pl was used to remove Poly tails with wrong bases added at the end due to impure dNTP, the self-written perl script FastQ_ReadFilterByLength.pl was used to filter too long or short reads, the fastx_collapser module in the FASTX Toolkit 0.0.13 software (the URL of the FASTX Toolkit 0.0.13 software is as follows: hannonlab.cshl.edu/fastx_toolkit/) was used to merge repeated sequences and to remove the reads with only one number. The purity of each component of the oligonucleotide was calculated according to the following formula: the ratio of each component (%)=the number of reads of the component/the sum of the number of reads of each component×100%.

The results are shown in Table 9 and FIG. From the results, it can be seen that of the obtained 9664589 oligonucleotide sequences, there were 7830352 oligonucleotide sequences that were completely identical to the oligonucleotide sequence (CAGAGCAGCTTGTCTTCTTC), and the ratio was 81.02%. Compared with the oligonucleotide sequence, there were 1331990 oligonucleotide sequences lacking a partial sequence at the 5' end, and the ratio was 13.78%; compared with the oligonucleotide sequence, there were 144439 oligonucleotide sequences lacking a partial sequence at the 3' end, and the ratio was 1.49%; compared with the oligonucleotide sequence, there were a total of 18697 oligonucleotide sequences lacking partial sequences both at the 5' end and 3' end, and the ratio was 0.19%; there were some other cases (such as insertion, deletion and incorporation of wrong bases, etc.) of oligonucleotide sequences with a total of 339111, and the ratio was 3.51%. The above results show that the method of the present invention can accurately and comprehensively analyze the content of each component in the oligonucleotide sequence and its ratio.

TABLE 9

| Data analysis results | | |
| --- | --- | --- |
| Category (compared with the oligonucleotide sequence) | Number (of sequences) | Ratio (%) |
| Completely identical | 7830352 | 81.02% |
| Lacking a partial sequence at the 5' end | 1331990 | 13.78% |
| Lacking a partial sequence at the 3' end | 144439 | 1.49% |
| Lacking partial sequences both at the 5' end and 3' end | 18697 | 0.19% |
| Other cases | 339111 | 3.51% |
| Total | 9664589 | |

Note:
The oligonucleotide sequence is CAGAGCAGCTTGTCTTCTTC.

3. Data Analysis
The ncbi-blast-2.2.28+software (the URL of ncbi-blast-2.2.28+software is as follows: ftp.ncbi.nlm.nih.gov/blast/executables/blast+/2.2.28/) was first used to align with the oligonucleotide reference sequence; a self-written script was used to parse the alignment results, standardize the parsed results, classify the standardized results, and finally count the classified results.

Table 10 shows the analysis results of the components with a content of greater than 0.1% and their contents. The analysis results of N−1 reads and N+1 reads are shown in Tables 11 and 12. In the tables, the oligonucleotide sequence and content of each component whose content is greater than 0.1%, the content and ratio of each component in N−1 reads and N+1 reads are shown.

TABLE 10

| Components with a content of greater than 0.1% and their contents | | |
| --- | --- | --- |
| Component No. | Component | Ratio (%) |
| 1-7830352 | CAGAGCAGCTTGTCTTCTTC | 81.02% |
| 2-209704 | GCTTGTCTTTCTTC | 2.17% |

TABLE 10 -continued

Components with a content of greater than 0.1% and their contents

| Component No. | Component | Ratio (%) |
|---|---|---|
| 3-204757 | AGAGCAGCTTGTCTTTCTTC | 2.12% |
| 4-182418 | CAGCTTGTCTTTCTTC | 1.89% |
| 5-165497 | GAGCAGCTTGTCTTTCTTC | 1.71% |
| 6-157170 | GCAGCTTGTCTTTCTTC | 1.63% |
| 7-154399 | AGCAGCTTGTCTTTCTTC | 1.60% |
| 8-133435 | CTTGTCTTTCTTC | 1.38% |
| 9-122557 | AGCTTGTCTTTCTTC | 1.27% |
| 10-85682 | CAGAGCAGCTTGTCTTTCTT | 0.89% |
| 11-34227 | CAGAGCAGCTTGTCTTTCTC | 0.35% |
| 12-18571 | CAGAGCAGCTTGTCTTTCT | 0.19% |
| 13-18146 | CAGAGCAGCTTGTCTTCTTC | 0.19% |
| 14-15125 | CAGAGAGCTTGTCTTTCTTC | 0.16% |
| 15-13947 | CGGAGCAGCTTGTCTTTCTC | 0.14% |
| 16-13400 | CTGAGCAGCTTGTCTTTCTTC | 0.14% |
| 17-11075 | CAGAGCAGCTTGTCTTTC | 0.11% |
| 18-10938 | CAAGCAGCTTGTCTTTCTTC | 0.11% |
| 19-9391 | CGAGCAGCTTGTCTTTCTTC | 0.10% |
| | Others | 2.83% |

TABLE 11

Analysis results of N − 1 reads

| No. | Category (compared with the oligonucleotide sequence) | Number of reads | Ratio (%) |
|---|---|---|---|
| 1 | Reads lacking some bases at the 5' end or 3' end | 290439 | 68.22% |
| 2 | Reads with incorrect bases | 2447 | 0.57% |
| 3 | Reads with missing bases in the middle | 76214 | |
| 4 | Reads with partial insertion or deletion at the 5' end or 3' end | 57425 | 17.9% |
| 5 | Reads with inserted bases | 137 | 13.49% |
| 6 | Total number of N − 1 reads | 425718 | 0.03% |

Note:
The oligonucleotide sequence is CAGAGCAGCTTGTCTTTCTTC.

TABLE 12

Analysis results of N + 1 reads

| No. | Category (compared with the oligonucleotide sequence) | Number of reads | Ratio (%) |
|---|---|---|---|
| 1 | Reads with incorrect bases | 73 | 0.56 |
| 2 | Reads with inserted bases | 8571 | 65.32 |
| 3 | Reads whose bases at the 5' end and 3' end cannot match | 4568 | 34.81 |
| 4 | Reads with missing bases in the middle | 0 | 0 |
| 5 | Total number of N + 1 reads | 13122 | |

Note:
The oligonucleotide sequence is CAGAGCAGCTTGTCTTTCTTC.

INDUSTRIAL APPLICATION

The present invention provides a method for analyzing impurities of an oligonucleotide sequence based on high-throughput sequencing. The method of the present invention comprises the following steps: constructing a high-throughput sequencing library for analysis of impurities of an oligonucleotide sequence; subjecting the high-throughput sequencing library to high-throughput sequencing, and analyzing the nucleotide sequence components according to the sequencing results; the sequence of the extension primer used in the construction of the high-throughput sequencing library consisting of the DNA molecule set forth in positions 1-22 of SEQ ID NO: 2 and N bases (A, T, C or G) in sequence; and N being an integer greater than or equal to 6. It is proved by experiments that the method for analyzing impurities of an oligonucleotide sequence based on high-throughput sequencing of the present invention can quickly, accurately, and comprehensively analyze the purity and content of each component in the oligonucleotide sequence.

What is claimed is:

1. A method for constructing a high-throughput sequencing library for analysis of impurities of an oligonucleotide sequence, comprising the following steps:
   1) Adding a poly tail to the 3' end of an oligonucleotide sequence to be detected to obtain a poly-tailed product;
   2) Performing reverse extension and amplification on the poly-tailed product to obtain a reverse extension and amplification product;
   the primers used for the reverse extension and amplification consisting of the oligonucleotide to be detected and an extension primer;
   the extension primer sequence consisting of the DNA molecule set forth in positions 1-22 of SEQ ID NO: 2 and N identical bases (A, T, C, or G) in sequence, wherein the N bases are complementary to the bases of the poly tail with N being an integer greater than or equal to 6;
   3) Precipitating the reverse extension and amplification product to obtain a precipitated product;
   4) Performing end repair, A-tailing reaction, adapter ligation and PCR amplification on the precipitated product sequentially to obtain a high-throughput sequencing library.

2. The method according to claim 1, wherein the extension primer sequence is the DNA molecule set forth in SEQ ID NO: 1, SEQ ID NO: 2, SEQ ID NO: 3 or SEQ ID NO: 4.

3. The method according to claim 2, wherein the extension primer sequence is the DNA molecule set forth in SEQ ID NO: 1.

4. The method according to claim 1, wherein the oligonucleotide is single-stranded DNA or double-stranded DNA.

5. The method according to claim 4, wherein the oligonucleotide is single-stranded DNA.

6. The method according to claim 1, wherein the length of the oligonucleotide is 8-120 bp.

7. A product, which is any one of the following a1)-a3):
   a1) the extension primer in claim 1;
   a2) a PCR reagent containing the extension primer of a1);
   a3) a kit containing the extension primer of a1) or the PCR reagent of a2).

8. The product according to claim 7, wherein the final concentration of the extension primer in the PCR reagent is 0.1-100 µM.

9. A method for analyzing impurities of an oligonucleotide sequence, comprising the following steps:
   (1) constructing a high-throughput sequencing library for analysis of impurities of an oligonucleotide sequence according to the method of claim 1;
   (2) subjecting the high-throughput sequencing library to high-throughput sequencing and analyzing the nucleotide sequence components according to the sequencing results.

10. A method for analyzing components of an artificially synthesized antisense oligodeoxynucleotide sequence for gene therapy or analyzing the purity and/or content of each component in an artificially synthesized antisense oligodeoxynucleotide sequence for gene therapy, comprising the following steps:
   (1) constructing a high-throughput sequencing library for analysis of impurities of an oligonucleotide sequence according to the method of claim 1;
   wherein, the oligonucleotide sequence are the artificially synthesized antisense oligodeoxynucleotide sequence for gene therapy;
   (2) subjecting the high-throughput sequencing library to high-throughput sequencing and analyzing the nucleotide sequence components according to the sequencing results.

* * * * *

SEQUENCE LISTING

<160> NUMBER OF SEQ ID NOS: 27

<210> SEQ ID NO 1
<211> LENGTH: 42
<212> TYPE: DNA
<213> ORGANISM: Artificial Sequence
<220> FEATURE:
<223> OTHER INFORMATION: Synthesized

<400> SEQUENCE: 1
gagacacgaa tagacggcac gatttttttt ttttttttt tt          42

<210> SEQ ID NO 2
<211> LENGTH: 42
<212> TYPE: DNA

```
<213> ORGANISM: Artificial Sequence
<220> FEATURE:
<223> OTHER INFORMATION: Synthesized

<400> SEQUENCE: 2
gagacacgaa tagacggcac gacccccccc cccccccccc cc                          42

<210> SEQ ID NO 3
<211> LENGTH: 42
<212> TYPE: DNA
<213> ORGANISM: Artificial Sequence
<220> FEATURE:
<223> OTHER INFORMATION: Synthesized

<400> SEQUENCE: 3
gagacacgaa tagacggcac gaaaaaaaaa aaaaaaaaaa aa                          42

<210> SEQ ID NO 4
<211> LENGTH: 42
<212> TYPE: DNA
<213> ORGANISM: Artificial Sequence
<220> FEATURE:
<223> OTHER INFORMATION: Synthesized

<400> SEQUENCE: 4
gagacacgaa tagacggcac gagggggggg gggggggggg gg                          42

<210> SEQ ID NO 5
<211> LENGTH: 21
<212> TYPE: DNA
<213> ORGANISM: Artificial Sequence
<220> FEATURE:
<223> OTHER INFORMATION: Synthesized

<400> SEQUENCE: 5
cagagcagct tgtctttctt c                                                 21

<210> SEQ ID NO 6
<211> LENGTH: 58
<212> TYPE: DNA
<213> ORGANISM: Artificial Sequence
<220> FEATURE:
<223> OTHER INFORMATION: Synthesized

<400> SEQUENCE: 6
aatgatacgg cgaccaccga gatctacact ctttccctac acgacgctct tccgatct         58

<210> SEQ ID NO 7
<211> LENGTH: 63
<212> TYPE: DNA
<213> ORGANISM: Artificial Sequence
<220> FEATURE:
<223> OTHER INFORMATION: Synthesized

<400> SEQUENCE: 7
gatcggaaga gcacacgtct gaactccagt cacacagtga tctcgtatgc cgtcttctgc       60
ttg                                                                     63

<210> SEQ ID NO 8
<211> LENGTH: 58
<212> TYPE: DNA
<213> ORGANISM: Artificial Sequence
<220> FEATURE:
<223> OTHER INFORMATION: Synthesized

<400> SEQUENCE: 8
```

```
aatgatacgg cgaccaccga gatctacact ctttccctac acgacgctct tccgatct    58
```

<210> SEQ ID NO 9
<211> LENGTH: 64
<212> TYPE: DNA
<213> ORGANISM: Artificial Sequence
<220> FEATURE:
<223> OTHER INFORMATION: Synthesized

<400> SEQUENCE: 9

```
caagcagaag acggcatacg agatcactgt gtgactggag ttcagacgtg tgctcttccg    60
atct                                                                 64
```

<210> SEQ ID NO 10
<211> LENGTH: 14
<212> TYPE: DNA
<213> ORGANISM: Artificial Sequence
<220> FEATURE:
<223> OTHER INFORMATION: Synthesized

<400> SEQUENCE: 10

```
gcttgtcttt cttc                                                     14
```

<210> SEQ ID NO 11
<211> LENGTH: 20
<212> TYPE: DNA
<213> ORGANISM: Artificial Sequence
<220> FEATURE:
<223> OTHER INFORMATION: Synthesized

<400> SEQUENCE: 11

```
agagcagctt gtctttcttc                                               20
```

<210> SEQ ID NO 12
<211> LENGTH: 16
<212> TYPE: DNA
<213> ORGANISM: Artificial Sequence
<220> FEATURE:
<223> OTHER INFORMATION: Synthesized

<400> SEQUENCE: 12

```
cagcttgtct ttcttc                                                   16
```

<210> SEQ ID NO 13
<211> LENGTH: 19
<212> TYPE: DNA
<213> ORGANISM: Artificial Sequence
<220> FEATURE:
<223> OTHER INFORMATION: Synthesized

<400> SEQUENCE: 13

```
gagcagcttg tctttcttc                                                19
```

<210> SEQ ID NO 14
<211> LENGTH: 17
<212> TYPE: DNA
<213> ORGANISM: Artificial Sequence
<220> FEATURE:
<223> OTHER INFORMATION: Synthesized

<400> SEQUENCE: 14

```
gcagcttgtc tttcttc                                                  17
```

<210> SEQ ID NO 15

```
<211> LENGTH: 18
<212> TYPE: DNA
<213> ORGANISM: Artificial Sequence
<220> FEATURE:
<223> OTHER INFORMATION: Synthesized

<400> SEQUENCE: 15
agcagcttgt ctttcttc                                                 18

<210> SEQ ID NO 16
<211> LENGTH: 13
<212> TYPE: DNA
<213> ORGANISM: Artificial Sequence
<220> FEATURE:
<223> OTHER INFORMATION: Synthesized

<400> SEQUENCE: 16
cttgtctttc ttc                                                      13

<210> SEQ ID NO 17
<211> LENGTH: 15
<212> TYPE: DNA
<213> ORGANISM: Artificial Sequence
<220> FEATURE:
<223> OTHER INFORMATION: Synthesized

<400> SEQUENCE: 17
agcttgtctt tcttc                                                    15

<210> SEQ ID NO 18
<211> LENGTH: 20
<212> TYPE: DNA
<213> ORGANISM: Artificial Sequence
<220> FEATURE:
<223> OTHER INFORMATION: Synthesized

<400> SEQUENCE: 18
cagagcagct tgtctttctt                                               20

<210> SEQ ID NO 19
<211> LENGTH: 20
<212> TYPE: DNA
<213> ORGANISM: Artificial Sequence
<220> FEATURE:
<223> OTHER INFORMATION: Synthesized

<400> SEQUENCE: 19
cagagcagct tgtctttctc                                               20

<210> SEQ ID NO 20
<211> LENGTH: 19
<212> TYPE: DNA
<213> ORGANISM: Artificial Sequence
<220> FEATURE:
<223> OTHER INFORMATION: Synthesized

<400> SEQUENCE: 20
cagagcagct tgtctttct                                                19

<210> SEQ ID NO 21
<211> LENGTH: 20
<212> TYPE: DNA
<213> ORGANISM: Artificial Sequence
<220> FEATURE:
<223> OTHER INFORMATION: Synthesized

<400> SEQUENCE: 21
```
cagagcagct tgtcttcttc                                                    20

<210> SEQ ID NO 22
<211> LENGTH: 20
<212> TYPE: DNA
<213> ORGANISM: Artificial Sequence
<220> FEATURE:
<223> OTHER INFORMATION: Synthesized

<400> SEQUENCE: 22
cagagagctt gtctttcttc                                                    20

<210> SEQ ID NO 23
<211> LENGTH: 21
<212> TYPE: DNA
<213> ORGANISM: Artificial Sequence
<220> FEATURE:
<223> OTHER INFORMATION: Synthesized

<400> SEQUENCE: 23
cggagcagct tgtctttctt c                                                  21

<210> SEQ ID NO 24
<211> LENGTH: 21
<212> TYPE: DNA
<213> ORGANISM: Artificial Sequence
<220> FEATURE:
<223> OTHER INFORMATION: Synthesized

<400> SEQUENCE: 24
ctgagcagct tgtctttctt c                                                  21

<210> SEQ ID NO 25
<211> LENGTH: 18
<212> TYPE: DNA
<213> ORGANISM: Artificial Sequence
<220> FEATURE:
<223> OTHER INFORMATION: Synthesized

<400> SEQUENCE: 25
cagagcagct tgtctttc                                                      18

<210> SEQ ID NO 26
<211> LENGTH: 20
<212> TYPE: DNA
<213> ORGANISM: Artificial Sequence
<220> FEATURE:
<223> OTHER INFORMATION: Synthesized

<400> SEQUENCE: 26
caagcagctt gtctttcttc                                                    20

<210> SEQ ID NO 27
<211> LENGTH: 20
<212> TYPE: DNA
<213> ORGANISM: Artificial Sequence
<220> FEATURE:
<223> OTHER INFORMATION: Synthesized

<400> SEQUENCE: 27
cgagcagctt gtctttcttc                                                    20